(12) United States Patent
Addison et al.

(10) Patent No.: US 9,579,411 B2
(45) Date of Patent: Feb. 28, 2017

(54) HYDROGEL WOUND DRESSINGS EXHIBITING REDUCED FIBER LOSSES IN USE

(75) Inventors: Deborah Addison, Keasden (GB); Simon William Bayliff, North Yorkshire (GB); Breda Mary Cullen, North Yorkshire (GB); Michelle Del Bono, Lancashire (GB); William Pigg, York (GB); Margaret Stedman, North Yorkshire (GB); Paul Howard Lowing, West Yorkshire (GB)

(73) Assignee: KCI USA, Inc., San Antonio, TX (US)

( * ) Notice: Subject to any disclaimer, the term of this patent is extended or adjusted under 35 U.S.C. 154(b) by 2437 days.

(21) Appl. No.: 12/373,619

(22) PCT Filed: Jul. 12, 2007

(86) PCT No.: PCT/GB2007/002616
§ 371 (c)(1),
(2), (4) Date: Nov. 17, 2009

(87) PCT Pub. No.: WO2008/007101
PCT Pub. Date: Jan. 17, 2008

(65) Prior Publication Data
US 2010/0063467 A1    Mar. 11, 2010

(30) Foreign Application Priority Data

Jul. 13, 2006 (GB) .................................... 0613939

(51) Int. Cl.
*A61F 13/53* (2006.01)
*A61L 15/46* (2006.01)
(Continued)

(52) U.S. Cl.
CPC .............. *A61L 15/28* (2013.01); *A61L 15/26* (2013.01); *A61L 15/34* (2013.01); *A61L 15/42* (2013.01); *A61L 15/50* (2013.01); *A61L 15/60* (2013.01)

(58) Field of Classification Search
USPC ........ 604/361, 365–368, 358, 378–383, 304, 604/308, 385.03; 156/60; 128/888, 898;
(Continued)

(56) References Cited

U.S. PATENT DOCUMENTS 778,813 A    12/1904 Taylor
2005/0054998 A1*    3/2005 Poccia et al. ................. 604/367

FOREIGN PATENT DOCUMENTS

DE    4407031    9/1995
EP    0251810    1/1988
(Continued)

OTHER PUBLICATIONS

International Search Report and Written Opinion; International Application No. PCT/GB2007/002616; International Filing Date Jul. 12, 2007; 9 pages.

*Primary Examiner* — Tatyana Zalukaeva
*Assistant Examiner* — Sara Sass

(57) ABSTRACT

A wound dressing comprising: a water-absorbent fabric comprising at least about 10 wt. % of hydrogel-forming absorbent fibers based on the dry weight of the fabric; and an adhesion-resistant, water-permeable wound contacting surface textile layer that is substantially continuously bonded to at least one surface of said fabric. The surface textile layer may be formed by surface treatment of the fabric, or by bonding a suitable textile web to the surface of the fabric.

7 Claims, 3 Drawing Sheets

(51) Int. Cl.
*A61L 15/28* (2006.01)
*A61L 15/26* (2006.01)
*A61L 15/34* (2006.01)
*A61L 15/42* (2006.01)
*A61L 15/50* (2006.01)
*A61L 15/60* (2006.01)

(58) Field of Classification Search
USPC .......................................... 602/41–43, 52, 56
See application file for complete search history.

(56) References Cited

FOREIGN PATENT DOCUMENTS

| | | |
|---|---|---|
| EP | 0450671 | 10/1991 |
| EP | 0275353 | 7/1998 |
| GB | 1430634 | 3/1976 |
| JP | 4263855 | 9/1992 |
| WO | WO03053584 | 7/2003 |
| WO | WO2006020213 | 2/2006 |
| WO | WO2008000701 | 1/2008 |

* cited by examiner

HYDROGEL WOUND DRESSINGS EXHIBITING REDUCED FIBER LOSSES IN USE

The present invention relates to wound dressings comprising hydrogel-forming absorbent fibers, wherein the dressings exhibit reduced fiber loss into wounds during use.

Wound dressings are known that comprise a wound contacting layer in the form of a nonwoven fabric comprising hydrogel-forming absorbent fibers. Typical hydrogel-forming absorbent fibers include polyacrylates, calcium alginate and sodium carboxymethylcellulose (NaCMC) fibers. These fibers absorb several times their own weight of wound fluid, and form a hydrogel with swelling. Alginate in particular also has a positive therapeutic effect on wound healing. However, most of these hydrogel-forming fibrous materials are not absorbed completely in vivo, and therefore it is desirable to avoid shedding of these fibers into the wound under treatment.

It is known to provide wound dressing materials in the form of a nonwoven fabric made up of a mixture of hydrogel-forming absorbent fibers and non-absorbent textile fibers, such as polyamide staple fibers. The non-absorbent textile fibers provide improved structural integrity and improved wicking properties to the fabric. However, the shedding of these non-absorbent textile fibers into wounds under treatment is also undesirable, since most of the textile fibers are not absorbable in vivo.

WO03/053584 describes wound dressing materials in the form of a nonwoven fabric made up of a mixture of hydrogel-forming absorbent fibers and non-absorbent textile fibers, in which some of the non-absorbent textile fibers are coated with silver to give the dressings antimicrobial properties. The silver-coated fibers have a dark color, and it is especially desirable to avoid shedding of these fibers into the wound under treatment because of the undesirable appearance of the dark fibers in the wound.

The shedding of fibers from a nonwoven textile layer into a wound can be reduced by providing a suitable top sheet (wound contacting sheet) over the textile layer in the wound dressing. For example, a top sheet in the form of a polymer film having apertures much smaller than the length of the textile fibers can be used as the top sheet. EP-A-0275353 describes dressings of this type comprising a top sheet formed of an elastomeric, soft, non-absorbent polyurethane film less than 50 micrometers thick, thermally bonded to a surface of the absorbent textile wound dressing, each perforation in the film having open areas equal to a circle having a diameter of 0.25 to 1.2 mm, the perforations being present in sufficient number, and so distributed, as to provide an open area in the range from 5% to 25% of the total area of the film.

However, the use of a separate top sheet reduces the therapeutic effectiveness of the hydrogel forming fibers and of the antimicrobial silver in the textile dressing, and also interferes with uptake of wound fluid from the wound and reduces conformability of the dressing.

It has now been found that the shedding of fibers from hydrogel textile dressings into a wound can be reduced by bonding a thin layer of an adhesion-resistant material directly to the wound facing surface of the hydrogel-containing fabric.

Accordingly, in a first aspect the present invention provides a wound dressing comprising: a water-absorbent fabric, wherein said fabric has dry basis weight of at least about 100 g/m$^2$ and comprises at least about 10 wt. % of hydrogel-forming absorbent fibers based on the dry weight of the fabric; and an adhesion-resistant, water-permeable wound contacting textile surface layer that is substantially continuously bonded to at least one surface of said fabric. Suitably, the fabric comprises at least about 20 wt. % of the hydrogel-forming fibers, for example from about 30 wt. % to about 50 wt. % of such fibers.

The term "hydrogel-forming fibers" refers to fibers that can absorb at least about twice their own weight of water, preferably at least about four times their own weight of water, to form a hydrogel. The fibers are normally insoluble in water. Suitable materials for the hydrogel-forming fibers include alginates, carboxymethylcelluloses, hydroxyethylcelluloses, polyacrylates, and hyaluronates. Preferred materials are calcium alginate and sodium carboxymethylcellulose and mixtures thereof.

Suitably; the fabric comprises at least about 10 wt. % based on the dry weight of the fabric of substantially non-water-absorbent textile fibers, and preferably it comprises at least about 20 wt. % of such fibers, for example from about 30 wt. % to about 60 wt. % of such fibers. Suitable non-absorbent textile fibers include polyamide fibers such as nylon fibers, polyolefin fibers, and viscose fibers.

Suitably, the fabric comprises (and may consist essentially of) a mixture of hydrogel-forming fibers and substantially non-absorbent textile fibers, wherein at least a fraction of the fibers are coated with silver to provide antimicrobial activity. Preferably, the silver coating is applied to the non-absorbent textile fibers. The term "fibers" herein generally refers to staple fibers, but it may refer to longer textile fibers. It does not refer to pulp fibers. In any case, the median length of the fibers used to form the fabric is generally at least about 10 mm. Suitably, the amount of silver in the fabric is from about 0.1% to about 10 wt. %, based on the dry weight of the fabric.

In certain embodiments, the adhesion-resistant textile surface layer has been formed by treating a surface layer of the web with a lubricant. That is to say, the fibers in the surface layer have the same composition as the body of the textile layer and form part of the same fabric, but are coated with a lubricant composition. The lubricant may be applied in solution in a suitable solvent, for example by spraying, and then dried. The lubricant penetrates only a short distance into the surface of the fabric layer, whereby it coats fibers near the surface of the fabric layer but not in the core of the fabric layer. In this way the lubricant does not significantly alter the absorbency or the porosity of the fabric.

The amount of lubricant that is applied in these embodiments is small. Typical amounts of dry lubricant per side of the fabric are from about 0.1 g/m$^2$ to about 20 g/m$^2$, preferably from about 0.5 g/m$^2$ to about 10 g/m$^2$, for example from about 1 g/m$^2$ to about 4 g/m$^2$.

The term "lubricant" refers generally to any substance that reduces the adherency of the fabric to the wound tissue. Generally, the lubricant is not soluble in water so that it is not washed off in the wound. Suitably, the lubricant comprises a silicone compound. Suitable silicone compounds comprise polyalkylsiloxanes, in particular polydimethylsiloxanes. In certain embodiments, the lubricant may be polymerised or cross-linked in situ. Other suitable lubricants are fluorocarbon compounds, for example perfluoroalkanes such as polytetrafluoroethylene (PTFE).

In other embodiments, the lubricant comprises a substance selected from the group consisting of medically acceptable lipids, mineral oils and waxes, and mixtures thereof. Suitably, the lubricant is hydrophobic. It has been found that the use of a hydrophobic lubricant gives enhanced fiber retention, without significantly reducing the rate or quantity of liquid that is absorbed by the dressing.

In other embodiments, the lubricant comprises a medically acceptable lubricating polymer. Preferred polymers are biopolymers such as collagen, gelatin, cellulose derivatives such as oxidized regenerated cellulose (ORC), and starch derivatives. In certain embodiments the polymer may be a mucopolysaccharide, for example hyaluronic acid (HA). HA functions in nature as a lubricant in joint fluid.

It is known from DE-A-4407031 to apply silicones as a hydrophobic surface finish on conventional fabrics for use in wound dressings. However, silicone coatings have not hitherto been suggested to reduce fiber loss from hydrogel absorbent fabrics.

JP-A-4263855 describes antimicrobial wound dressings comprising a thin layer of a hydrogel that is coated with a hydrophobic silicone material. The purpose of the hydrogel is to maintain adequate humidity at the wound surface.

In alternative embodiments, the adhesion resistant surface textile layer comprises a non-adherent textile web having a basis weight of from about 2 to about 100 g/m2 that is directly bonded to the surface of the fabric. The composition of the fibers making up the textile web is different from that of the fibers making up the absorbent fabric. In particular, the surface textile web generally does not comprise any gel-forming fibers.

The surface textile web may be a woven or knitted fabric, but it is preferably a nonwoven fabric, more preferably a thermally-bonded nonwoven fabric comprising thermoplastic fibers. Examples of suitable thermoplastic fibers include polyamide, polyester and polypropylene. A woven or knitted or non-bonded nonwoven textile preferably consists of continuous filament yarn to minimise the possibility of textile fibers becoming detached and remaining behind on removal from a wound. Other types of nonwoven fabric may also advantageously consist of continuous filament yarn; in particular, a thermally spunbonded fabric may be used. The basis weight of the surface textile layer is preferably in the range from 5 to 80, more preferably from 10 to 50, g/m². The surface textile layer should be suitable for medical applications, and be susceptible to conventional sterilisation procedures such as exposure to ethylene oxide or to electron beam or gamma-ray irradiation.

Suitably, the non-adherent surface textile web comprises thermoplastic fibers, and the surface textile layer has been bonded to the water-absorbent fabric by thermal bonding, such as melt bonding, optionally also with compression.

In certain embodiments, the non-adherent surface textile web may comprise fibers that have been coated with a non-adherent composition prior to lamination with the absorbent fabric. The non-adherent composition may be a lubricant as hereinbefore described. For example, the web may be a gauze coated with a paraffinic material (so-called "tulle gras"). Suitable webs include cellulose acetate fabrics coated with petrolatum, such as those available from Johnson & Johnson under the Registered Trade Mark ADAPTIC. Other suitable webs include viscose fabrics coated with silicone, such as those available from Johnson & Johnson under the Registered Trade Mark N-A ULTRA.

Suitably, the wound dressing according to the present invention is sterile and packaged in a microorganism-impermeable container.

Specific embodiments of the present invention will now be described further, by way of example, with reference to the accompanying drawings, in which.

Figure 1:
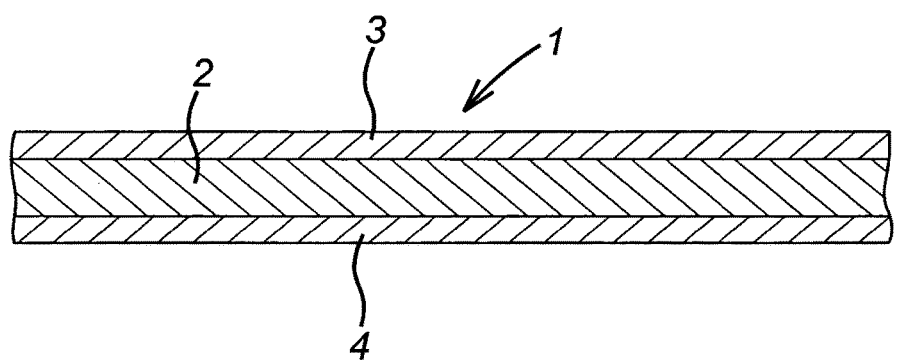
FIG. 1 shows a schematic cross-section through a wound dressing according to the present invention.

Referring to FIG. 1, the dressing 1 comprises a fabric layer 2 containing hydrogel-forming fibers and non-absorbent textile fibers, some of which are coated with metallic silver. The dressing further comprises adhesion-resistant nonwoven textile webs 3,4 (the thickness of which is exaggerated in the Figure) continuously bonded over the upper and lower surfaces of the fabric layer 2.

EXAMPLE 1

The fabric layer is a calcium alginate needled felt dressing incorporating silver-coated nylon fibers. The composition is as follows: calcium alginate and carboxymethyl cellulose (CMC) fibers 60% and silver coated nylon 40%. The basis weight of the fabric layer is about 150 g/m², and the uncompressed thickness of the fabric layer is about 2 mm. The fabric layer is commercially available from Johnson & Johnson under the Registered Trade Mark SILVERCEL.

The adhesion-resistant nonwoven web is formed from a layer of M1590 heat laminating material obtained from Freudenberg Vliesstoffe KG. It comprises 80% of an aliphatic non-cyclic co-polyamide (6/66.6/12-copolyamide, CAS number 26777-62-8), and 20% of polyetherester block copolyamide in which the polyetherester comprises a polyether block of medium molecular weight and the polyamide block is aliphatic and non-cyclic. The basis weight of the web is only about 10 g/m². This gives the layer a high porosity for water uptake from the wound.

The nonwoven web 2 was bonded to the fabric layer 1 by heating and compression. Suitable conditions are 116-127° C., press time 10-14 seconds, and pressure 150-300 kPa.

EXAMPLE 2

A dressing according to the invention was prepared as described in Example 1, except that bonding of the textile surface layer to the fabric body was achieved without compression, by placing the laminate in an oven at 150° C. for 10 minutes.

EXAMPLE 3

A dressing according to the invention was prepared as described in Example 2, except that the textile surface layer had a basis weight of 20 g/m².

EXAMPLES 4-10

Silicone-coated hydrogel fiber fabrics were prepared from a SILVERCEL fabric containing hydrogel-forming fibers as described in Example 1.

The silicone coating was made by first mixing together the two silicone components (SILOPREN RTV 2K Gel AC3293 components A and B supplied by GE BAYER) and then dissolving the mixture in acetone to assist spraying. Acetone concentration was 20-35% based on the weight of the mixture (hexane can also be used). The silicone coating was applied to both sides of the fabric in the following amounts (total dry weight of silicone—i.e. divide by two for the coating density per side of the fabric):

Example 4 4 g/m$^2$
Example 5 8 g/m$^2$
Example 6 14 g/m$^2$
Example 7 20 g/m$^2$
Example 8 21 g/m$^2$
Example 9 24 g/m$^2$
Example 10 26 g/m$^2$

EXAMPLES 11-12

Lubricant-coated hydrogel fiber fabrics were prepared from a SILVERCEL fabric containing hydrogel-forming fibers as described in Example 1 by spraying the surfaces of the fabric with a medically acceptable mineral oil. Two different coating weights were used.

EXAMPLE 13

A lubricant-coated hydrogel fiber fabric was prepared from a SILVERCEL fabric containing hydrogel-forming fibers as described in Example 1 by spraying the surfaces of the fabric with a solution of Hyaluronic acid.

REFERENCE EXAMPLE 1

Measurements of fiber loss, adherency and absorbency as detailed below were also carried out on a reference sample of SILVERCEL fabric as described in Example 1, without any coating.

REFERENCE EXAMPLE 2

Measurements of adherency and absorbency as detailed below were also carried out on a reference sample of AQUACEL Ag fabric supplied by. AQUACEL Ag is a needle-bonded nonwoven fabric formed from carboxymethylcellulose gel-forming fibers and containing silver in ionic form bonded to the CMC. There is no coating on the surfaces of the fabric.

REFERENCE EXAMPLE 3

Measurements of adherency and absorbency as detailed below were also carried out on a reference sample of a wound dressing made by heat-bonding a vacuum-perforated ethylene methyl acrylate (EMA) film onto the surfaces of a fabric layer as described in Example 1. The characteristics of the EMA film were as described in EP-A-1168998, the entire content of which is incorporated herein by reference. The lamination was performed at about 150° C., between sheets of siliconized release paper.

REFERENCE EXAMPLE 4

Measurements of adherency and absorbency as detailed below were also carried out on a reference sample of a wound dressing made by heat-bonding a thermoplastic net of base weight 10-88 g/m2, hole size 100-1400 micrometers and thickness 0.05-0.3 mm obtained from Delstar Technologies Inc. of Bristol, UK onto the surfaces of a fabric layer as described in Example 1. The lamination was performed at about 150° C., between sheets of siliconized release paper.
Procedure 1
A qualitative assessment of fiber loss was performed by applying adhesive tape to the surface of the dressing with the adhesive side down at an applied pressure of about 5 g/cm2, followed by lifting the tape from the dressing and observing the amount of fiber attached to the tape. It was found that fiber shedding onto the tape of the dressing of Example 1 was very much less than that observed with Reference Example 1.
Procedure 2
A Fibrin Clot Adhesion Test used as an in-vitro method to evaluate likely fiber loss to the wound surface. A fibrin clot is formed from bovine plasma fibrinogen, phosphate buffered saline, bovine serum albumin and bovine thrombin. The formed clot is placed between two samples of the dressing, dried and pulled apart in an Instron force measurement device. The force required to pull the dressings apart is measured.

Figure 2:
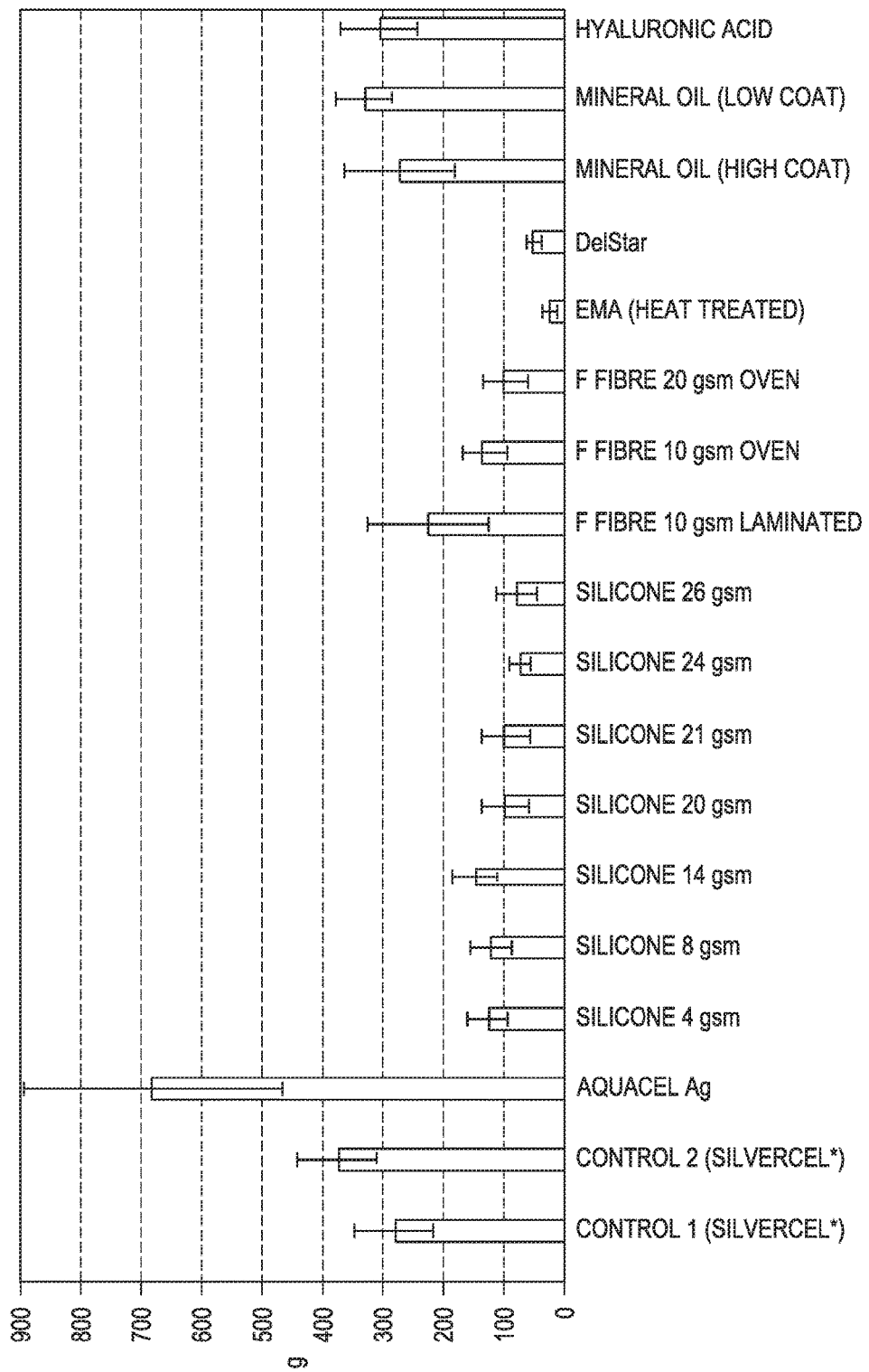
FIG. 2 shows a bar chart of measured peak fibrin clot adhesion force for wound dressings according to the invention and for certain reference dressings.

The peak force required to pull the dressings apart is shown graphically in FIG. 2 for the above Examples. It can be seen that all of the examples exhibit a reduced fibrin clot adhesion force. The effect is especially marked for the siliconized samples. The effect is observed down to very low coating weights of the silicone composition.
Procedure 3

The wound fluid absorbency of the example dressings was evaluated as follows. The method was based on the absorbency test on Alginate dressings described in the British Pharmacopoeia 1993, Addendum 1995, Page 1706.

Figure 3:
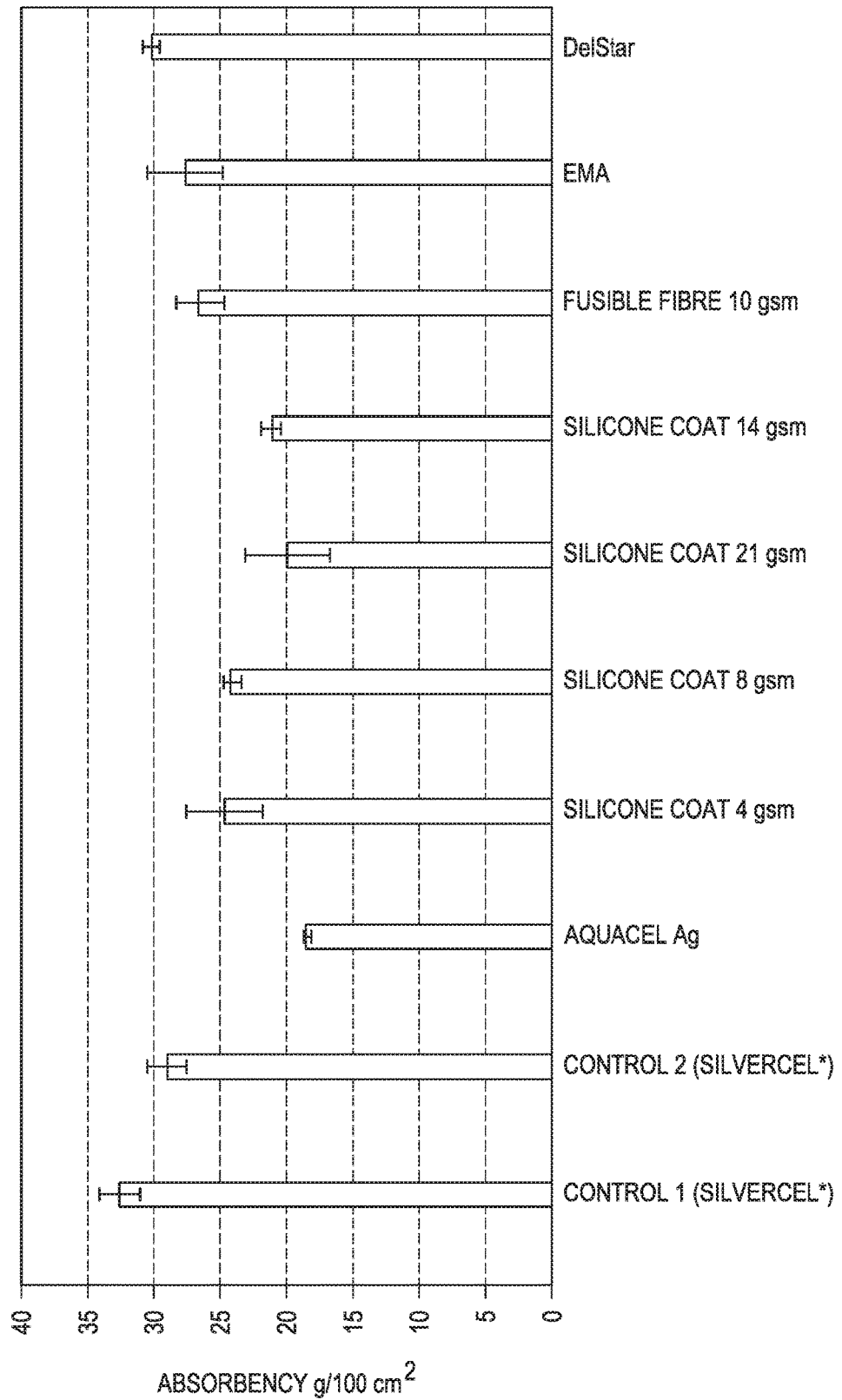
FIG. 3 shows a bar chart of measured liquid absorbency for wound dressings according to the invention and for certain reference dressings.

Briefly, a 5 cm×5 cm sample was excised form a dressing and weighed. This sample was placed in a Petri dish. The sample is then submerged in a solution of sodium chloride and calcium chloride that had been heated to 37° C. The material was suspended for 30 seconds using a set of forceps before the sample was weighed. This test was repeated on a further 4 samples. The absorbency was then expressed as the average weight of solution retained per 100 cm$^2$. The results are shown in FIG. 3. It can be seen that the dressings according to the invention all have absorbency similar to that of the unmodified SILVERCEL dressings.
Procedure 4

The silver release into simulated wound fluid at 37° C. over a period of 3 days of the dressings according to the above examples was evaluated as follows.

The simulated wound fluid was a solution containing:

$$\left.\begin{array}{l} 0.013M\ CaCl_2, \\ 0.2M\ NaCl \\ 0.04M\ \textit{Tris}, \\ 2\%\ Bovine\ Albumin \end{array}\right\} \text{at pH 7.5}$$

The wound dressings were tested over 3 days. At each 24 hour time-point, the dressings were re-challenged with a fresh amount of simulated wound fluid equivalent to 5 ml/2.5×2.5 cm$^2$. Each batch was analysed in triplicate.

Analysis was performed against a silver standard curve prepared in simulated wound fluid was carried out using the Perkin Elmer A Analyst 200 Atomic Absorption Spectrometer Standards of known concentration were prepared in the same simulated wound fluid as used for the dressings. Calibration curves were prepared daily.

The results showed that the dressings according to the present invention gave substantially the same rate and amount of silver release as the untreated SILVERCEL dressings.

The above embodiments have been described for the purpose of illustration only. Many other embodiments falling within the scope of the present invention will be apparent to the skilled reader.

The invention claimed is:

1. A wound dressing comprising:
   a water-absorbent fabric comprising at least 10 wt. % of hydrogel-forming absorbent fibers based on the dry weight of the fabric; and
   an adhesion-resistant, water-permeable wound contacting surface textile layer that is substantially continuously bonded to at least one surface of said fabric, wherein the fabric comprises at least 10 wt. % based on the dry weight of the fabric of substantially non-water-absorbent textile fibers and wherein the fabric comprises a mixture of the hydrogel-forming fibers and the substantially non-water-absorbent textile fibers, and wherein at least a fraction of the non-water-absorbent fibers are coated with silver.

2. A wound dressing according to claim 1, wherein said adhesion resistant surface textile layer has been formed by treating a surface layer of the fabric with a lubricant.

3. A wound dressing according to claim 2, wherein the lubricant comprises a silicone compound or a fluorocarbon.

4. A wound dressing according to claim 2, wherein the lubricant comprises a substance selected from the group consisting of medically acceptable lipids, mineral oils, mucopolysaccharides, and mixtures thereof.

5. A wound dressing according to claim 1, wherein said adhesion resistant surface layer comprises a nonwoven textile web having a basis weight of from 2 to 100 $g/m^2$ that is continuously bonded to said surface of the fabric.

6. A wound dressing according to claim 5, wherein said nonwoven textile web comprises thermofusible fibers, and the textile web has been bonded to the water-absorbent textile web by melt bonding.

7. A wound dressing according to claim 1, which is sterile and packaged in a microorganism-impermeable container.

* * * * *